United States Patent [19]

Lacourciere et al.

[11] Patent Number: 4,932,410
[45] Date of Patent: Jun. 12, 1990

[54] DUAL MEMBRANE MOUNTING FOR TRANSCUTANEOUS OXYGEN AND CARBON DIOXIDE SENSOR

[75] Inventors: William J. Lacourciere, Chesire, Conn.; David R. Rich, San Diego, Calif.

[73] Assignee: Novametrix Medical Systems, Inc., Wallingford, Conn.

[21] Appl. No.: 259,217

[22] Filed: Oct. 18, 1988

[51] Int. Cl.$^5$ .............................................. A61B 5/00
[52] U.S. Cl. .................................. 128/635; 204/403; 204/412; 204/415
[58] Field of Search ................ 128/635; 204/403, 412, 204/415

[56] References Cited

U.S. PATENT DOCUMENTS

| 4,197,853 | 4/1980 | Parker | 128/635 |
| 4,280,505 | 7/1981 | Dali et al. | 128/635 |
| 4,789,453 | 12/1988 | Eberhard et al. | 128/635 |
| 4,836,907 | 6/1989 | Pedersen | 128/635 X |

FOREIGN PATENT DOCUMENTS

| 0088748 | 7/1980 | Japan | 128/635 |
| 0128945 | 6/1986 | Japan | 128/635 |
| 8102831 | 10/1981 | World Int. Prop. O. | 128/635 |

*Primary Examiner*—Lee S. Cohen
*Attorney, Agent, or Firm*—Howard F. Mandelbaum

[57] ABSTRACT

A transcutaneous sensor probe having dual sensing electrodes responsive to the effects of two different transcutaneous gases on an ion solution separated from the skin surface by a selectively permeable seal having respective regions overlying the corresponding electrodes. The permeable seal is mounted on a removable fixation ring which is indexed to ensure alignment between each region of the seal and its respective electrode when the fixation ring is connected to the electrode housing.

9 Claims, 2 Drawing Sheets

DUAL MEMBRANE MOUNTING FOR TRANSCUTANEOUS OXYGEN AND CARBON DIOXIDE SENSOR

BACKGROUND OF THE INVENTION

This invention relates to the use of a single sensor probe and monitor to detect and measure transcutaneous gases at the surface of the skin. More specifically, this invention relates to a sensor probe having dual sensing electrodes responsive to the effects of two different transcutaneous gases on an ion solution separated from the skin surface by a selectively permeable seal having respective regions covering the corresponding electrodes.

It is known in the art to measure oxygen and carbon dioxide in the blood non-invasively by measuring the partial pressures of oxygen ($pO_2$) and carbon dioxide ($pCO_2$) in the adjacent body tissue. The measurement is done by means of a transcutaneous gas sensor having a electrodes covered by a selectively permeable seal in the form of a membrane. In the case of oxygen, the sensor is a Clark electrode, named after its inventor, Leland Clark. In a Clark electrode, an electrolyte is placed above the membrane and bridges the two electrodes. The membrane face of the sensor is placed against the skin of a patient and a voltage is applied across the electrodes. Oxygen in the tissue diffuses through the skin, through the membrane and through the electrolyte to the electrodes where it is electrochemically reduced by the applied voltage across the electrodes to cause an electric current to flow between the electrodes. The current produced by the reduction reaction, which can be metered and recorded, is a measure of the oxygen in the tissue.

In the case of carbon dioxide ($CO_2$), the sensor is a Stow-Severinghaus electrode, named after its inventors, R.W. Stow and John Severinghaus. A Stow-Severinghaus electrode (sometimes called a Severinghaus electrode) is a pH electrode, i.e., it measures the pH of a solution. When $CO_2$ is dissolved in the electrolyte it affects the pH of the solution. A pH electrode connected to a pH meter can measure the pH. Since pH is proportional to $pCO_2$, the pH electrode can also measure $CO_2$.

In a Severinghaus electrode, as in the Clark electrode used to measure oxygen passing through the skin, an electrolyte is placed above the membrane and bridges the two electrodes. The membrane face of the sensor is placed against the skin. Unlike the oxygen sensing Clark electrode, in the Severinghaus electrode used to measure $pCO_2$, no voltage is applied across the electrodes. Carbon dioxide in the blood diffuses through the skin, through the membrane and through the electrolyte. The effect of the $CO_2$ dissolving in the electrolyte changes the pH of the electrolyte thereby inducing a voltage (much like a battery) which is measured as an indication of the $pCO_2$ in the body tissue.

It is also known to measure both oxygen and carbon dioxide with a single sensor probe utilizing a single measuring electrode (cathode). This results in a compromise since no single measuring electrode is optimum for use in measuring both oxygen and carbon dioxide. Hence the use of two separate measuring electrodes, each optimized for its respective gas, e.g., oxygen and carbon dioxide, has been found preferable.

Moreover, it is known to facilitate removal and replacement of the membrane in an oxygen or carbon dioxide electrode sensor probe through the use of a detachable fixation ring as set forth in U.S. Pat. No. 4,280,505 to Dali. When a single active electrode is employed in a single sensor probe to measure oxygen or carbon dioxide, or both oxygen and carbon dioxide, no problem is presented with respect to the use of a fixation ring. When two active electrodes are employed in a single sensor probe to measure oxygen and carbon dioxide respectively and simultaneously a problem is presented with respect to the use of a fixation ring. Since carbon dioxide electrodes differ from oxygen electrodes, and the membrane material best suited as permeable to oxygen is different from the membrane material best suited as permeable to carbon dioxide, the membrane assembly cannot be randomly angularly positioned with respect to the electrodes as is permissible where a single gas measuring electrode is used.

The present invention solves the aforementioned problem in providing for a sensor for monitoring first and second transcutaneous gases with the use of a single probe having dual measuring electrodes engaging respective different selectively permeable seal materials, e.g., membrane materials which can be mounted by means of a fixation ring that allows the membrane materials to reproducibly engage their respective measuring electrodes thereby accomplishing lateral and angular alignment with respect to eccentrically mounted oxygen and carbon dioxide electrodes.

SUMMARY OF THE INVENTION

A sensor for monitoring first and second transcutaneous gases at the surface of the skin including, an electrode housing, a first electrode mounted in the electrode housing for detecting the first gas, a second electrode mounted in the electrode housing for detecting the second gas, a seal supporting housing releasably mountable on the electrode housing, a selectively permeable seal mounted on the seal supporting housing, the seal having a first region permeable to the first gas and a second region permeable to the second gas, the first and second electrodes being angularly displaced from an electrode housing index by the same degree to which the first and second permeable seal regions are respectively angularly displaced from a seal supporting housing index, and cooperative interlocking means on the electrode housing and on the seal supporting housing for positively mounting the seal supporting housing on the electrode housing with the first region of the seal in engagement with the first electrode and the second region of the seal in engagement with the second electrode wherein the indexes positively limit relative movement therebetween.

It is therefore an object of the invention to provide a sensor for monitoring first and second transcutaneous gases at the surface of the skin.

It is another object of the invention to provide a sensor for monitoring first and second transcutaneous gases at the surface of the skin by permitting the gases to diffuse through two adjacent respective regions of a permeable seal, each region being permeable to a different one of the gases.

It is still another object of the invention to provide a sensor for monitoring first and second transcutaneous gases at the surface of the skin wherein the permeable seal is readily removed from and replaced on the electrode supporting sensor structure.

It is a further object of the invention to provide a sensor for monitoring first and second transcutaneous gases at the surface of the skin wherein the seal regions automatically align with their respective electrodes when replaced on the electrode supporting sensor structure.

Other and further objects of the invention will be apparent from the following description of a preferred embodiment of the invention in which like reference numerals are used to designate like parts in the various views.

DESCRIPTION OF THE PREFERRED EMBODIMENT

Figure 1:
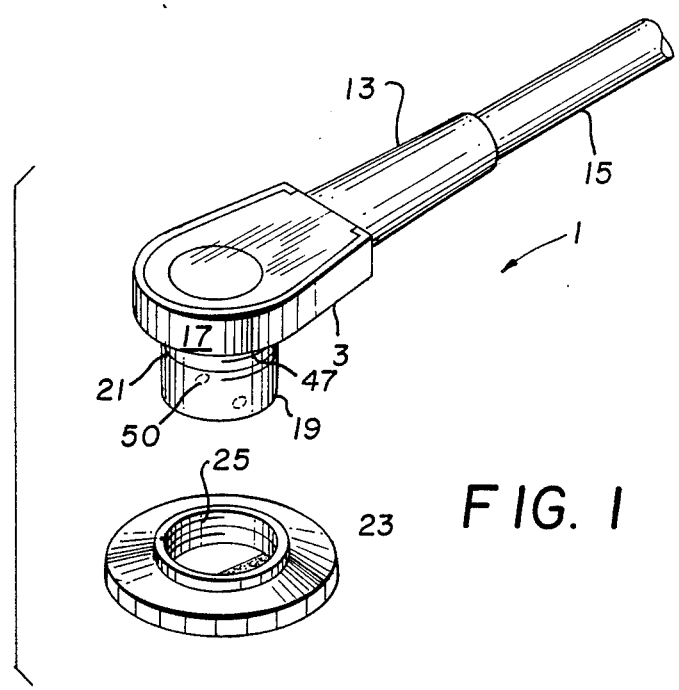
FIG. 1 is a perspective view of the apparatus of the preferred embodiment of the invention.
Figure 2:
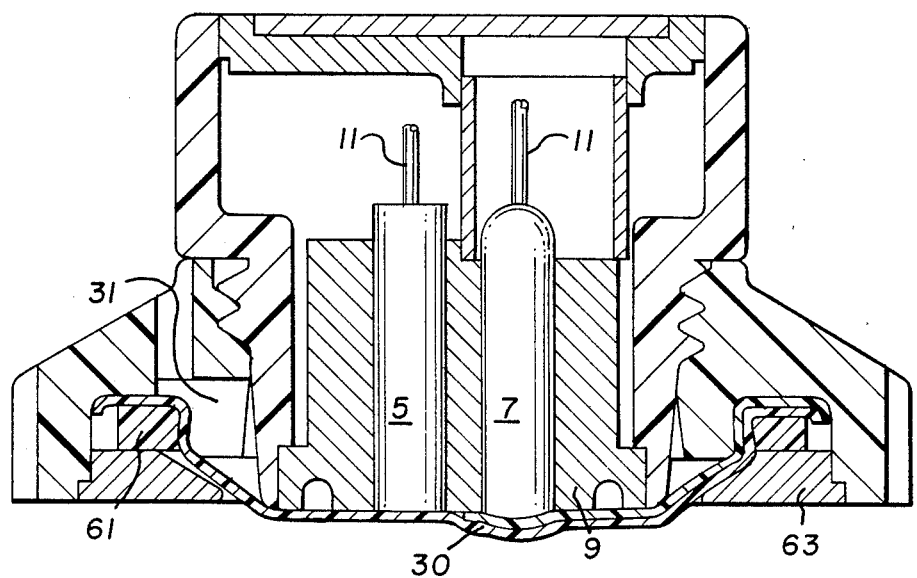
FIG. 2 is a sectional elevation view of the apparatus of the preferred embodiment of the invention.

Referring now to FIGS. 1 and 2, there is shown a transcutaneous gas sensor probe 1 including a housing 3 in which there is mounted a downwardly extending oxygen electrode 5 and a downwardly extending carbon dioxide electrode 7, each of which serves as a cathode. A common anode 9 serves as a reference electrode. The oxygen electrode 5 can include a solid glass cylindrical rod in which a platinum wire is axially disposed. The carbon dioxide electrode 7 can include a hollow cylindrical glass tube terminated with pH glass and partially filled with an electrolyte solution in which a silver-silver chloride wire is axially disposed.

Respective wire conductors 11 extend from the oxygen electrode 5 and carbon dioxide electrode 7 into a cable 15 and through a bore in an integral strain relief 13 that extends from the electrode housing 3. The cable 15 is terminated in a suitable connector (not shown) for mating with the input of a transcutaneous gas monitor.

The housing 3 has an enlarged cylindrical upper portion 17 and a smaller diameter lower portion 19 with threads 21 on its exterior. A fixation ring 23 which serves as a permeable seal bearing housing has interior threads 25 for mounting the fixation ring 23 on the electrode housing 3.

Figure 4:
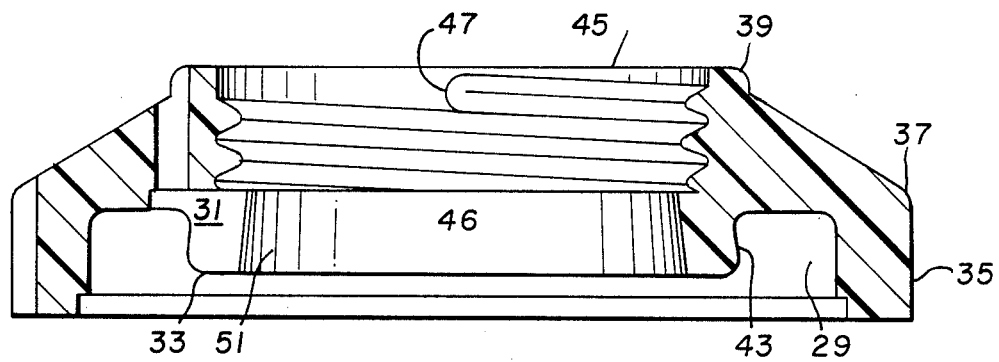
FIG. 4 is a sectional elevation view of a component of the apparatus of the preferred embodiment of the invention.

As can be seen in FIG. 4 the fixation ring 23 has a downward facing circumferential channel 29 surrounding a concentric protuberance 31 having a downward facing planar face 33. A circular ridge 35, the inner wall of which defines the outer wall of the channel 29 extends axially downwardly beyond the protuberance 31 and upwardly to a shoulder 37 at which it tapers inwardly as it continues upwardly to a circular upwardly directed planar face 39. The inner wall of the channel 29 is defined by the outer wall 43 of the circular protuberance 31 which tapers downwardly and outwardly at an angle of about six degrees.

An axial circular bore 45 extends the entire length of the fixation ring 23 which in the preferred embodiment of the invention is 0.2 inches. Beginning just below, i.e., 0.005 inches, the upwardly directed planar face 39 in the interior cylindrical wall of the bore 45 is an integral single pitch thread 46 which in the preferred embodiment of the invention is 32 threads per inch. The thread 46 extends downwardly for one half the length of the fixation ring 23, i.e., for 0.1 inches.

A minimal taper is provided at the start of the thread to form a convex abutment 47 for engaging a complementary concave abutment 49 at the terminus of the thread 50 on the exterior cylindrical wall 19 of the electrode housing 3. Beneath the thread 46 in the bore 45 of the fixation ring 23 the interior wall 51 of the bore 55 tapers downwardly and outwardly at an angle of approximately six degrees.

Figure 3:
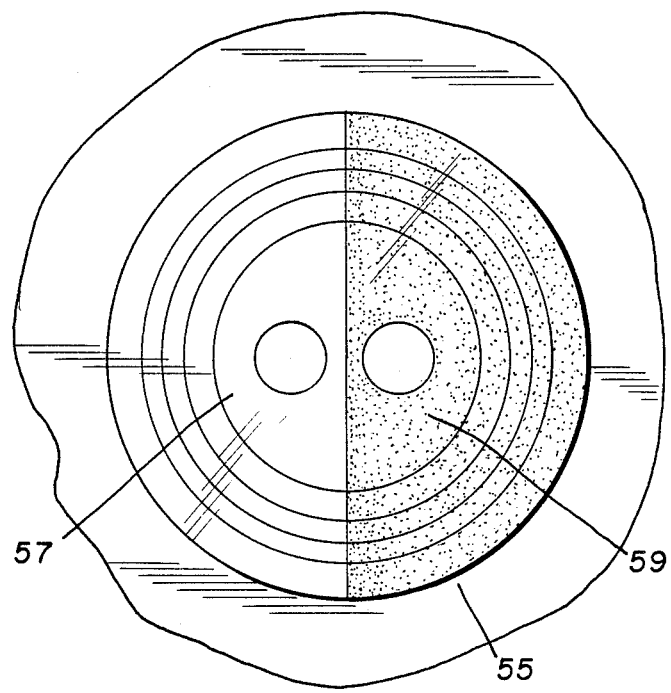
FIG. 3 is a plan view of the apparatus of the preferred embodiment of the invention.

Referring to FIG. 3, a permeable seal in the form of a compound circular membrane 55 having a diameter greater than that of the downwardly directed circular protuberance 31 of the fixation ring 23 is mounted on the underside of the protuberance 31 by means of an elastomeric 0-ring 61. The circular membrane has a diameter large enough to extend over the inner wall 43 of the channel 29, and preferably well into the channel 29.

In the preferred embodiment of the invention, the membrane 29 is formed from a circular layer of material of one mil thickness sold under the popular trademark Teflon. Overlying one half of the Teflon membrane is a semi-circular layer of material of one half mil thickness sold under the trademark Cuprophane.

The Teflon material is permeable to both oxygen and carbon dioxide. The cuprophane material absorbs electrolyte and acts as a reservoir to increase the volume of electrolyte in the vicinity of the carbon dioxide electrode. In order for accurate measurements to be made, it is necessary that the oxygen electrode be covered only by the Teflon-only region 57 of the compound membrane whereas the carbon dioxide electrode must be covered by the Teflon-cuprophane region 59 as sown in FIG. 3.

The abutment 47 at the beginning of the thread on the fixation ring or any other fixed point away from the center of the fixation ring 29 can serve as an index for orienting the compound membrane 55 so that the oxygen electrode 5 is covered only by the Teflon-only region 57 of the compound membrane while the carbon dioxide electrode 7 is covered by the Teflon-Cuprophane region 59. This is done with reference to the angular displacements of the oxygen and carbon dioxide electrodes 5,7 from a corresponding index point, e.g., the terminus 49 of the thread 50, on the electrode housing 3. In the preferred embodiment of the invention, the oxygen and carbon dioxide electrodes 5,7 are diametrically opposite one another. The compound membrane 55 is placed over the fixation ring protuberance 31 and oriented so that the angular distance between a radius of the fixation ring 23 passing through its index point 47 and a radius passing through the Teflon-only region 57 is equal to the angular distance between a radius of the electrode housing 3 passing through its index point 49 and a radius passing through the oxygen electrode 5. Similarly, the angular distance between a radius of the fixation ring 23 passing through its index point 47 and a radius passing through the Teflon-Cuprophane region 59 is equal to the angular distance between a radius of the electrode housing 3 passing through its index point 49 and a radius passing through the carbon dioxide electrode 7. Once so positioned, the compound membrane 55 is fixed laterally and angularly in place by means of the elastomeric 0-ring 61 which is placed over the compound membrane 55 and protuberance 31. A planar ring 63 can then be fitted into the channel 29 to form a planar bearing surface for engaging the skin at the measuring site.

It is to be understood and appreciated that alterations, modifications and variations of and to the preferred embodiment described herein may be made without departing from the spirit and scope of the invention which is defined in the following claims. For example, although the preferred embodiment of the invention has been described as utilizing the beginning and terminus of the fixation ring and electrode housing threads as respective indexes, another projection or recess, or other visible marking can be employed. Moreover, the oxygen and carbon dioxide electrodes need not be on a common diameter provided that they are angularly displaced from each other.

What is claimed is:

1. A sensor for monitoring first and second transcutaneous gases at the surface of the skin comprising,
    an electrode housing,
    a first electrode mounted in said electrode housing for detecting said second gas,
    a second electrode mounted in said electrode housing for detecting said second gas,
    a seal supporting housing releasably mountable on said electrode housing, each of said seal supporting housing and said electrode housing including a respective indexing means for limiting relative movement therebetween,
    a selectively permeable seal mounted on said seal supporting housing, said seal having a first region permeable to said first gas and a second region permeable to said second gas,
    and cooperative interlocking means on said electrode housing and on said seal supporting housing for positively mounting said seal supporting housing on said electrode housing with said first region of said seal in engagement with said first electrode and said second region of said seal in engagement with said second electrode, said first and second electrodes being angularly displaced from said electrode housing indexing means by the same degree to which said first and second permeable seal regions are respectively angularly displaced from said seal supporting housing indexing means.

2. A sensor for monitoring first and second transcutaneous gases at the surface of the skin according to claim 1 wherein said cooperative interlocking means comprises a single pitch attachment thread on said seal supporting housing and a complimentary single pitch attachment thread on said electrode housing.

3. A sensor for monitoring first and second transcutaneous gases at the surface of the skin according to claim 2 wherein said seal supporting housing indexing means comprises a first abutment and said electrode housing indexing means comprises a second abutment adapted to engage said first abutment for positively limiting relative rotation therebetween.

4. A sensor for monitoring first and second transcutaneous gases at the surface of the skin according to claim 3 wherein said first abutment is integral with said seal supporting housing thread and said second abutment is integral with said electrode housing thread.

5. A sensor for monitoring first and second transcutaneous gases at the surface of the skin according to claim 1 further comprising elastomeric means for releasably attaching said permeable seal to said seal supporting housing for permitting adjustment of the relative angle between said permeable seal and said seal supporting housing.

6. A method of preparing, for monitoring first and second transcutaneous gases at the surface of the skin, a sensor having a first electrode for detecting said first gas and a second electrode for detecting said second gas comprising
    mounting a selectively permeable seal having a first region permeable to said first gas and a second region permeable to said second gas relative to an index on a seal supporting housing and
    connecting said seal supporting housing to said sensor with said index in a predetermined position relative to said first and second electrodes so that said first and second electrodes are angularly displaced from said index by the same degree to which said first and second permeable seal regions are respectively angularly displaced from said index, and limiting relative movement therebetween, whereby said first and second regions of said permeable seal are in alignment with said first and second electrodes, respectively.

7. A method according to claim 7 wherein said seal supporting housing is threaded onto said sensor and said index comprises the beginning of a thread.

8. A method according to claim 7 wherein said seal supporting housing is threaded onto said sensor and said index comprises the terminus of a thread.

9. A method according to claim 7 wherein said seal supporting housing is threaded onto said sensor and the beginning of the thread on one of said sensor and said seal supporting housing engages the terminus of the other of the thread on one of said sensor and said seal supporting housing to positively fix the relative angular positions of said sensor and said seal bearing housing with said first and second regions of said permeable seal aligned with said first and second electrodes, respectively.

* * * * *